United States Patent [19]

Kawamata et al.

[11] Patent Number: 4,614,796

[45] Date of Patent: Sep. 30, 1986

[54] LIPOSOME AND METHOD OF MANUFACTURE THEREFOR

[75] Inventors: Masanobu Kawamata; Koichi Ushimaru; Shuji Yamane, all of Kyoto, Japan

[73] Assignee: Nippon Shinyaku Co., Ltd., Japan

[21] Appl. No.: 478,903

[22] Filed: Mar. 25, 1983

[51] Int. Cl.[4] ...................... C07J 0/00; A61K 31/705
[52] U.S. Cl. ............................................ 536/5; 514/26
[58] Field of Search ................... 424/180, 182, 16, 35, 424/38; 536/5

[56] References Cited

U.S. PATENT DOCUMENTS

| | | | |
|---|---|---|---|
| 3,887,698 | 6/1975 | McConnell et al. | 424/12 |
| 3,991,186 | 11/1976 | Murai et al. | 424/182 |
| 4,129,649 | 12/1978 | Inoue et al. | 424/182 |
| 4,188,379 | 2/1980 | Pegel | 424/182 |
| 4,193,983 | 3/1980 | Ullman et al. | 424/12 |
| 4,333,926 | 6/1982 | Ohata et al. | 424/182 |

OTHER PUBLICATIONS

Arrowsmith et al., The Release and Clearance of an I.M, Administered Liposome Formulation of Steroids, Chem. Abstracts 97: 11746b (1981).
Bittman et al., Stopped-Flow Kinetic and Equilibrium Studies of Filipin III Binding to Sterols, Chem. Abstracts 80: 142121r (1974).
Dingle, Articular Damage in Arthritis and its Control, Chem. Abstracts 89: 53693x (1978).
Umezawa et al., Amperometric Detection of Glucose Released from Immune Lysis of Glucose Loaded Liposome, Chem. Abstracts 96: 140866u (1982).
Nippon Shinyaku Co., Ltd., Liposomes Containing Sterol Glucosides, Chem. Abstracts 99: 58903g (1983).
Chemical Abstracts 84: 53732f (1976).
Chemical Abstracts 85: 73898p (1976).
Chemical Abstracts 92: 169146n (1980).

*Primary Examiner*—Ethel G. Love
*Attorney, Agent, or Firm*—Jacobs & Jacobs

[57] ABSTRACT

Liposomes of steryl glucosides and/or steryl glucoside monopalmitates are useful for hemostatic, vascular stabilization and anti-shock effects, particularly in the form of injectable solutions.

15 Claims, No Drawings

LIPOSOME AND METHOD OF MANUFACTURE THEREFOR

The present invention relates to a liposome of a steryl glucoside or steryl glucoside monopalmitate as well as a method of manufacturing the same.

Steryl glucosides and steryl glucoside monopalmitates are contained in plants and they can be extracted and separated, mostly in the form of a mixture of $\beta$-sitosteryl-$\beta$-D-glucoside, stigmasteryl-$\beta$-D-glucoside and campesteryl glucoside, as well as fatty acid esters thereof, from various natural materials such as, for example, soybean, cotton seed, gram, chickpea, grapefruit grounds, and the like by the method of, for example, T. Kiribuchi, et al. disclosed in *Agricultural Biological Chemistry*, volume 30, number 8, pages 770 to 778 (1966). In order to provide steryl glucoside, the mixture obtained by the above-mentioned method is hydrolyzed with an alkali. Steryl glucosides obtained from this hydrolysis are converted to the steryl glucosides monopalmitates by known methods.

The ratio of these steryl glucosides will vary depending upon the plant from which the compounds are extracted, as can be seen from Table 1 below:

The amounts of steryl glucosides extracted and separated from plants are given in Table 1.

TABLE 1

|  | $\beta$-Sitosteryl-$\beta$-D-glucoside | Stigmasteryl-$\beta$-D-glucoside | Campesteryl-$\beta$-D-glucoside |
|---|---|---|---|
| Soybean | 56% | 23% | 21% |
| Cotton Seed | 96% | 4% | 0% |
| Gram or Chickpea | 87% | 0% | 3% |
| Grapefruit Pulp | 84% | 9% | 7% |

Steryl glucosides can be synthesized from plant sterols obtained in the form of $\beta$-sitosterol, stigmasterol, campesterol or a mixture thereof by known methods, such as, for example, that reported in *Chemische Berichte*, volume 105, pages 1097 to 1121. The resulting steryl glucosides can be readily converted to their monopalmitates.

Steryl glucosides are soluble in pyridine, somewhat soluble in dioxane, sparingly soluble in alcohols and ketones, and nearly insoluble in usual organic solvents such as hydrocarbons and halogen-containing solvents as well as in water.

There is no substantial difference in the physical and chemical properties of steryl glucosides even when the sterol moieties differ or even in mixtures thereof extracted from plants. On the other hand, steryl glucoside monopalmitates are soluble in non-polar solvents, somewhat soluble in alcohols and nearly insoluble in water. There is no difference in the physical and chemical properties of steryl glucoside monopalmitates even when the sterol moieties differ or even in mixtures thereof extracted from plants.

Steryl glucosides and steryl glucoside monopalmitates are useful for their hemostatic action, vascular stabilizing action and anti-shock action as disclosed in Japanese Examined Patent Publication No. Sho-54-11369 and Japanese Unexamined Patent Publication No. Sho-53-109954 and are thus useful pharmaceuticals. It is desirable to use these compounds in the form of injectable solutions in view of their pharmacological activity but, because of their insolubility in water, it has been impossible to dissolve them in aqueous solvents to prepare injectable solutions.

Attempts have been made to make injectable formulations of these compounds by dissolving them in non-aqueous solvents or making them into suspensions. However, in the former case, solubilities of the compounds in propylene glycol, Macrogol and vegetable oils, which are frequently used as solvents for injectable solutions, are low and it is not possible to obtain the desired concentrations. In the latter case, preparation of an injection suspension is possible, but when it is injected in vivo the transport of the compound from the site of injection is so slow that the desired pharmaceutical effect cannot be obtained. Neither possibility provides the desired injectable solutions.

Since conventional techniques of preparing injectable solution of barely soluble compounds do not provide injectable solutions of steryl glucosides and of steryl glucoside monopalmitates, special techniques are required. There has previously been proposed a means of water solubilization of these compounds by the use of hydrophilic solvents and solubilizing agents as disclosed, for example, in Japanese Examined Patent Publication Nos. Sho-53-31210 and Sho-53-20567. According to such methods, however, there are still several areas in which improvement is needed. They are for example, as follows:

(1) Since the affinity of stearyl glucosides and stearyl glucoside monopalmitates to water is very low, comparatively large amounts of solvents or surface active agents are necessary for solubilizing such compounds in water.

(2) When an ampoule containing the solution is sterilized by heating, surface active agents in the solution separate out and adhere to the wall of the ampoule.

(3) When injected intravenously, the pharmacological effect of the compound is affected by the solubilizing agent used. In fact, the desired effect is not achieved by the use of solubilizing agents except for a few, such as HCO-60 (Trademark) (polyoxyethylene 60 moles and hardened castor oil).

The present invention is based on extensive studies conducted to find an injectable solution that can be easily subjected to sterilization by heating, that contains high concentrations of active ingredient suitable for use as a hemostat, and as vascular stabilizers and anti-shock agents where high doses are required, and that affords a reliable pharmaceutical effect even by intravenous injection. As a result, the present invention fulfills these objects by including the active compounds in a liposome. Thus, the present invention provides a liposome which comprises steryl glucosides and steryl glucoside monopalmitates, and a method of manufacture thereof.

Examples of the use of a liposome as a carrier for pharmaceuticals have recently been found in the literature and its structure, composition and methods of manufacture and are found in various reviews. For instance, Tyrell, D. H., et al. *Biochmica et Biophysica Acta MR* 457, pages 259 to 302 (1976), Flender, J. H., et al. *Life Science*, 20(7), pages 1109–1020 (1977).

Liposomes are generally obtained in the following forms. Thus, a solution of a lipid in chloroform is placed in an eggplant type flask, chloroform is evaporated therefrom so that a thin membrane of the lipid is formed on the wall of the flask, then a buffer and an aqueous solution of the pharmaceutical agent are added thereto, and the lipid membrane is taken off from the wall by stirring, whereupon an aqueous solution of the pharmaceutical agent is included in the resulting small globe or vehicle.

Previously, it has been necessary to remove pharmaceuticals not incorporated in the liposome by gel filtration or by ultra-centrifugation. Furthermore, since the liposome is in the above form, an aqueous solution of the pharmaceutical in the liposome diffuses out to the outer aqueous layer within a short time even when the liposome is separated from the free pharmaceuticals, so that the liposome cannot be used as a practical pharmaceutical preparation.

However, we have unexpectedly found that steryl glucosides and steryl glucoside monopalmitates have a strong affinity with the lipid that constitutes the liposome, and therefore that these compounds can be included in a liposome lipid. Thus, the present invention provides a liposome composition in which steryl glucosides or steryl glucoside monopalmitates are included in the lipid. This composition may be obtained by dissolving a lipid in chloroform, adding steryl glucosides or steryl glucoside monopalmitates thereto, and if necessary, adding a membrane stabilizer (such as cholesterol) or a charging agent to assist in their dissolution, and then evaporating chloroform therefrom, and admixing the resulting material with physiological saline solution or buffer solution with stirring or subjecting the material to ultrasonic mixing.

Examples of lipids useful in the present invention are natural lipids such as lecithin, sphingolipid phosphoglycerides, gangliosides, etc. or synthetic lipids such as dimyristoyl-dipalmitoyl-, distearyl-, and dioleylphosphatidyl choline, etc. Natural or synthetic lecithins are presently preferred. Examples of stabilizers for a liposome membrane are cholesterol, $\beta$-sitosterol, stigmasterol, campesterol or mixed sterols extracted from plant materials. Examples of charging agents are stearylamine which charges positive electric charge and phosphatidic acid and dicetylphosphoric acid which charge negative electric charges.

Examples of steryl glucosides useful in the present invention are $\beta$-sitosteryl-$\beta$-D-glucoside, stigmasteryl-$\beta$-D-glucoside, campesteryl-$\beta$-D-glucoside, cholesteryl-$\beta$-D-glucoside and a mixture of steryl glucosides mainly composed of the above steryl glucosides extracted from plant materials. Examples of steryl glucoside monopalmitates useful in this invention are 6-monopalmitates of the abovementioned steryl glucosides.

It is preferred to use one to ten parts (most preferably three to five parts) of the lipid, 0.1 to 5 parts (most preferably 0.3 to 2 parts) of a sterol, and 0.05 to 0.5 parts of charging agent (when present) per part by weight of the steryl glucoside or steryl glucoside monopalmitate. Depending upon the strength and time for stirring and ultrasonic homogenization, multilamella or unilamella liposomes are obtained.

The liposome of the invention containing steryl glucosides or steryl glucoside monopalmitate is administered to mammals, including humans, by parenteral route and has the following advantages:

(1) Due to the use of as small an amount as three to five parts by weight of lipid to one part by weight of the active ingredient, it is possible to provide an injectable solution suitable for intravenous injection.

(2) It is possible to prepare an injectable solution containing even five or more percent of active ingredient and, therefore, it is possible to offer injectable solutions not only for hemostatic purposes, but also for use in vascular stabilization and anti-shock, which require high administration doses.

(3) The composition of the present invention provides reliable pharmacological effects even by intravenous injection.

(4) Sterilization by heating can be done easily. Besides these advantages, the liposome of the present invention has remarkable storage properties, when filled in an ampoule together with nitrogen gas and stored in the dark, it is stable at least for two years at room temperatures, giving no changes in appearance or in concentration.

Representative examples of the present invention are as follows:

EXAMPLE 1

Yolk lecithin (20 mg) is placed in a 50 ml eggplant form flask, the contents are dissolved in 2 ml of chloroform, then 5 mg of $\beta$-sitosteryl-$\beta$-D-glucoside and 2 mg of cholesterol are dissolved therein, and chloroform is evaporated therefrom on a steam bath at 30° C. using a rotary evaporator. Nitrogen gas is blown into the residue for ten minutes, which is then dried for six hours in a vacuum desiccator, after which 5 ml of physiological saline solution is added thereto, and homogenized for three minutes under a nitrogen stream using a probe type ultrasonic wave homogenizer (Choompa Kogyo Co., 25 KHz, 150W) to give a nearly transparent, pale yellow liquid. This is subjected to a sterile filtration using millipore filter GS type to give a filtrate in which 99.6% of $\beta$-sitosteryl-$\beta$-D-glucoside as compared with its amount before filtration is identified. The filtrate is filled in a 5 ml ampoule together with a nitrogen gas and subjected to a sterilization in an autoclave at 120° C. for twenty minutes. Separation of neither the active ingredient nor the lipid is observed after the sterilization. When the injectable solution thus formed is stored in the dark, neither separation of foreign matters nor a lowering of the concentration of the active ingredient was observed after more than two years at room temperature.

Both this injectable solution and a blank solution prepared by removing the active ingredient were administered intravenously to mice (ten mice to a group). The tails of the mice were cut 1 cm from the end with a surgical knife, soaked in water, and the time elapsed until the bleeding stopped was measured (cf. Motohashi, et al., Tokyo *Jikeikai Medical Journal*, 75(5), 1008, 1959) to evaluate the pharmacological activity of the injectable solutions of the invention. The results are shown in Table 2, and it is apparent that, while the average hemostatic time in the blank or control group was 14.7±0.82 minutes, the group that was administered 0.2 mg/kg of the injectable solution of the present invention showed a hemostatic time of 12.3±0.27 minutes. Thus, there is a significant difference within a level of $P<0.01$ and the effectiveness of the present injectable solution for intravenous injection has been proven.

EXAMPLE 2

Dipalmitoyl lecithin (20 mg), 10 mg of $\beta$-sitosteryl-$\beta$-D-glucoside monopalmitate and 5 mg of cholesterol are dissolved in 3 ml of chloroform and the mixture is evaporated in vacuo on a water bath of 30° C. using a rotary evaporator. Nitrogen gas is blown into the resulting residue for ten minutes and it is dried for more than six hours in a vacuum desiccator. To this is added 5 ml of phosphate buffer of pH 6.2 (prepared by dissolving 1.8 grams of trisodium phosphate, 6.4 grams of sodium dihydrogen phosphate and 5.1 grams of sodium chloride in a distilled water for injection to make one liter) and the mixture is homogenized for three minutes using a probe type ultrasonic wave homogenizer to provide a slightly turbid liposome solution. This is filtered with a millipore filter HA type to give a filtrate in which 99.2% of β-sitosteryl-β-D-glucoside monopalmitate is contained. The filtrate is filled in an ampoule together with nitrogen gas and sterilized with high pressure steam at 120° C. for twenty minutes in an autoclave. The pharmacological effect of the resulting injectable solution by intravenous route is shown in Table 2.

EXAMPLE 3

In a 50 ml eggplant type flask are placed 4 mg of dioleyl phosphatidyl choline and 4 mg of dipalmitoyl phosphatidyl choline, the mixture is dissolved in 2 ml of chloroform, then 3 mg of cholesteryl-β-D-glucoside and 1 mg of cholesterol are dissolved therein, and chloroform is evaporated therefrom on a water bath of 30° C. using a rotary evaporator. This is further treated as in Example 1 to afford 5 ml of liposome solution containing 3 mg of cholesteryl-β-D-glucoside. The pharmacological activity of the solution is shown in Table 2.

EXAMPLE 4

In a 50 ml eggplant type flask is placed 15 mg of dipalmitoyl lecithin dissolved in 2 ml of chloroform, then 5 mg of stigmasteryl-β-D-glucoside, 5 mg of stigmasterol and 1 mg of stearylamine are dissolved therein, and chloroform is evaporated therefrom on a water bath of 30° C. using an evaporator. Then this is treated by the same way as Example 2 to give 5 ml of liposome solution having positive charge containing 5 mg of stigmasteryl-β-D-glucoside. The pharmacological activity of the resulting injection solution is shown in Table 2.

EXAMPLE 5

The procedure of Example 4 is repeated except that in place of the 1 mg of stearylamine in Example 4, 1 kg of dicetylphosphoric acid issued. This gives 5 ml of liposome solution with a negative charge containing 5 mg of stigmasteryl-β-D-glucoside. The pharmacological activity of the injectable solution is shown in Table 2.

EXAMPLE 6

Yolk lecithin (200 mg) is placed in a 100 ml eggplant type flask, it is dissolved in 5 ml of chloroform, then 50 mg of steryl glucoside and 25 mg of cholesterol extracted from soybean are dissolved therein, and chloroform is evaporated therefrom in vacuo on a water bath of 30° C. using a rotary evaporator. Nitrogen gas is blown onto the residue for ten minutes and dried for six hours in a vacuum desiccator. To this is added 5 ml of phosphate buffer which is used in Example 2, homogenized for five minutes under a nitrogen stream using a probe type ultrasonic wave homogenizer to give a slightly turbid liposome solution. This is filtered using a millipore filter HA type to give a filtrate containing 98.2 percent of steryl glucoside. Then this is treated by the same way as Example 1 to give 5 ml of liposome solution containing 50 mg of steryl glucoside. The pharmacological activity of this injectable solution is shown in Table 2.

EXAMPLE 7

In a 100 ml eggplant type flask is placed 200 mg of yolk lecithin, dissolved by addition of 5 ml of chloroform, 50 of cholesterol and 50 mg of steryl glucoside monopalmitates extracted from cotton seed are dissolved therein, and then treated as in Example 6 to give 5 ml of liposome solution containing 50 mg of steryl glucoside monopalmitates extracted from cotton seed. The pharmacological activity of this injectable solution is shown in Table 2.

From Table 2, it is quite apparent that the compositions of the present invention have a pharmacological activity by intravenous injection.

TABLE 2

Pharmacological Activities of Liposome Injection Solutions

| No. | Composition according to | Route of Administration | Time Required For Bleeding To Stop At Doses of 0.1 to 0.4 mg/kg (minutes). | | | |
|---|---|---|---|---|---|---|
| | | | 0.4 mg/kg | 0.2 mg/kg | 0.1 mg/kg | Blank |
| 1 | Example 1 | intravenous | 11.1 ± 1.55** | 11.7 ± 0.87** | 14.0 ± 1.13 | 14.7 ± 0.82 |
| 2 | Example 2 | intravenous | 9.5 ± 0.91** | 11.1 ± 1.12** | 13.8 ± 1.02 | " |
| 3 | Example 3 | intraneous | 11.3 ± 1.20** | 11.4 ± 0.78** | 12.0 ± 0.96 | " |
| 4 | Example 4 | intraneous | 10.8 ± 0.91** | 11.6 ± 0.80** | 13.3 ± 1.12 | " |
| 5 | Example 5 | intravenous | 11.2 ± 0.81** | 12.2 ± 0.75* | 12.8 ± 1.00 | " |
| 6 | Example 6 | intraveous | 9.7 ± 0.88** | 10.9 ± 1.15** | 12.1 ± 0.80 | 14.2 ± 0.95 |
| 7 | Example 7 | intraveous | 11.6 ± 0.73** | 11.2 ± 0.82** | 12.5 ± 0.96 | " |

*p < 0.05
**p < 0.01
Note:
The dosages refer to the amount of active ingredient administered, i.e. steryl glucoside or steryl glucoside monopalmitate.

In addition to the lipsome per se, the present invention also provides a pharmaceutical composition, useful as a hemostat, a vascular stabilizer or an anti-shock agent, which comprises a liposome of a steryl glucoside and/or a steryl glucoside monopalmitate, water and a lipid in which said steryl glucoside and/or said steryl glucoside monopalmitate is present in a hemostatically, vascular stabilizing or anti-shock effective amount.

The active compounds of the invention, namely the steryl glucoside and/or steryl glucoside monopalmitates, are known per se as being effective to achieve a hemostatic, vascular stabilization and anti-shock effect in humans and other animals. See U.S. Pat. No. 4,333,926, issued June 8, 1982 to K. Ohata et al., which is hereby incorporated herein by reference thereto. The liposomes of the present invention may thus be administered to humans and other animals in need thereof by the same routes and in the same dosages as described in U.S. Pat. No. 4,333,926. Preferably, however, the liposome is administered in the form of an injectable solution comprising the liposome. Such injectable solutions are preferably provided in heat sterilized 5 ml ampoules, each containing, for example, from 1 to 5 mg of active compound. Useful dosages for hemostatic purposes may be 0.5 to 1 ampoule containing 1 mg of active compound one or more times a day. Useful dosages for vascular stabilization may be one ampoule containing 5 mg of active compound one or more times a day. Useful dosages for anti-shock may be two ampoules containing 5 mg of active compound one or more times a day.

We claim:

1. A liposome comprising a steryl glucoside and/or a steryl glucoside monopalmitate, water and a lipid selected from the group consisting of natural and synthetic phosphatidyl cholines.

2. The liposome according to claim 1, in the form of simple lamella.

3. The liposome according to claim 1, in the form of multi-layered lamella.

4. The liposome according to claim 1, in which said natural phosphatidyl choline is yolk lecithin.

5. The liposome according to claim 1, in which said synthetic phosphatidyl choline is selected from the group consisting of dimyristoil phosphatidyl choline, dipalmitoyl phosphatidyl choline, distearyl phosphatidyl choline and dioleyl phosphatidyl choline and mixtures thereof.

6. The liposome according to claim 1, in which a sterol is included as a stabilizer for the liposome.

7. The liposome according to claim 6, in which said sterol is selected from the group consisting of cholesterol, β-sitosterol, stigmasterol and campesterol and mixtures thereof.

8. The liposome according to claim 1, including a charging agent that donates a positive charge.

9. The liposome according to claim 8, in which said charging agent donating a positive charge is stearylamine.

10. The liposome according to claim 1, in which the liposome contains a charging agent that donates a negative charge.

11. The liposome according to claim 10, in which the charging agent is phosphatidic acid or dicetylphosphoric acid.

12. The liposome according to claim 1, in which said steryl glucoside is selected from the group consisting of -β-sitosteryl-β-D-glucoside, stigmasteryl-β-D-glucoside, campesteryl-β-D-glucoside and cholesteryl-β-D-glucoside and a mixture thereof and said sterylglucoside monopalmitate is a monopalmitate of said steryl glucoside.

13. The liposome according to claim 1, in which said steryl glucoside is selected from the group consisting of -β-sitosteryl-β-D-glucoside, stigmasteryl-β-D-glucoside, campesteryl-β-D-glucoside and cholesteryl-β-D-glucoside and a mixture thereof and said sterylglucoside monopalmitate is a monopalmitate of said steryl glucoside.

14. The liposome according to claim 6, in which said steryl glucoside is selected from the group consisting of -β-sitosteryl-β-D-glucoside, stigmasteryl-β-D-glucoside, campesteryl-β-D-glucoside and cholesteryl-β-D-glucoside and a mixture thereof and said sterylglucoside monopalmitate is a monopalmitate of said steryl glucoside.

15. The liposome according to claim 8, in which said steryl glucoside is selected from the group consisting of -β-sitosteryl-β-D-glucoside, stigmasteryl-β-D-glucoside, campesteryl-β-D-glucoside and cholesteryl-β-D-glucoside and a mixture thereof and said sterylglucoside monopalmitate is a monopalmitate of said steryl glucoside.

* * * * *